United States Patent
Komiya et al.

Patent Number: 6,040,198
Date of Patent: Mar. 21, 2000

[54] ELEMENT CONCENTRATION MEASURING METHOD AND APPARATUS, AND SEMICONDUCTOR DEVICE FABRICATION METHOD AND APPARATUS

[75] Inventors: Satoshi Komiya; Naoki Awaji; Shunji Kashiwagi, all of Kawasaki, Japan

[73] Assignee: Fujitsu Limited, Kawasaki, Japan

[21] Appl. No.: 09/018,852

[22] Filed: Feb. 4, 1998

Related U.S. Application Data

[63] Continuation-in-part of application No. 08/757,622, Nov. 27, 1996, Pat. No. 5,740,226.

[30] Foreign Application Priority Data

Nov. 30, 1995 [JP] Japan .................................. 7-312441
Jun. 9, 1997 [JP] Japan .................................. 9-151226

[51] Int. Cl.$^7$ .................................................. G01R 31/26
[52] U.S. Cl. .................................. 438/16; 378/45; 378/83
[58] Field of Search .......................... 438/16, 7; 378/45, 378/83, 88

[56] References Cited

U.S. PATENT DOCUMENTS

| | | | |
|---|---|---|---|
| 4,959,848 | 9/1990 | Parobek | 378/46 |
| 5,003,569 | 3/1991 | Okada et al. | 378/70 |
| 5,148,457 | 9/1992 | Kubota et al. | 378/70 |
| 5,430,786 | 7/1995 | Komatsu et al. | 378/45 |
| 5,619,548 | 4/1997 | Koppel | 378/70 |
| 5,742,658 | 4/1998 | Tiffin et al. | 378/44 |

FOREIGN PATENT DOCUMENTS 07260712 10/1995 Japan .

OTHER PUBLICATIONS

U.S. application No. 08/757,622, Komiya et al., filed Nov. 27, 1996.

*Primary Examiner*—John F. Niebling
*Assistant Examiner*—John Murphy
*Attorney, Agent, or Firm*—Staas & Halsey LLP

[57] ABSTRACT

X-rays are irradiated to a sample to be measured including at least one layer of film formed on a substrate; an interference oscillation curve of the X-rays incident on the sample to be measured is measured; and a concentration of an element adhered on a surface of the sample to be measured and/or segregated in an interface of the film is measured. The interference oscillation curve is fitted to an analysis formula expressing an X-ray reflectance to thereby determining a density of a region of the sample to be measured, where the element is adhered or is segregated, and a concentration of the element is computed based on the density.

7 Claims, 12 Drawing Sheets

ELEMENT CONCENTRATION MEASURING METHOD AND APPARATUS, AND SEMICONDUCTOR DEVICE FABRICATION METHOD AND APPARATUS

CROSS REFERENCE TO RELATED APPLICATION

This application is a continuation-in-part of Ser. No. 08/757,622, filed Nov. 27, 1996, now U.S. Pat. No. 5,740,226.

BACKGROUND OF THE INVENTION

The present invention relates to an analyzing method using X-ray reflectance measurement, more specifically to an element concentration measuring method and apparatus for measuring concentrations of elements adhered on a surface of a sample-to-be-measured and/or segregated on an interface of films, and a method and apparatus for fabricating a semiconductor device.

With the recent larger scale and higher integration of semiconductor devices, insulation films, metal films, dielectric films, magnetic films, etc. have been further thinned. What significant here is how to control composite elements segregated on surfaces of samples or interfaces of multi-layer films.

For example, in a semiconductor device including a MOS transistor, to control diffusion of boron (B) in the silicon substrate and obtain low interface state it is often conducted that the gate insulation film of silicon oxide film is formed and then heat-treated in an $N_2O$ or an NO atmosphere to introduce nitrogen into the interface between the silicon substrate and the gate insulation film. Toproduce sufficient effect it is necessary to accurately quantify a concentration of nitrogen to be introduced.

Impurities, such as boron, phosphorus (P), antimony (Sb), arsenic (As), are segregated In high concentrations between the silicon substrates and the gate insulation films may affect electric characteristics of the semiconductor devices. It is also important to control segregation quantities of such segregated impurities.

It is very effective to quantify impurities adhered and segregated on surfaces of samples as well as interfaces of the samples so as to improve device characteristics and inline process control.

In measuring elements adhered or segregated on such interfaces and surfaces SIMS (Secondary Ion Mass Spectroscopy) is dominantly used. SIMS is a method for quantifying concentrations of traces of elements contained in a sample by irradiating primary ions to the sample to sputter the surface of the sample and mass-analyzing secondary ions in the sputtered particles.

SIMS is a measuring means which enables the measurement with high sensitivity but destructively measures a depth-wide impurity concentration distribution by sputtering the surface of a sample. It is difficult to uniformly sputter a sample surface so that measured impurity profiles cannot be abruptly changed at the interfaces. Accordingly SIMS is not usable in line process control, to which non-destructive inspection is essential. It is impossible for SIMS to quantify impurity concentrations in a very thin region. The SIMS measurement costs much.

Measuring techniques other than SIMS are AES (Auger Electron Spectroscopy, XPS (X-ray Photoelectron Spectroscopy), fluorescence analysis, ellipsometry, etc. are known.

In AES and XPS, profiles cannot be also abruptly changed at the interface regions due to the sputtering as well as SIMS and escape lengths (about 1 nm) of measured electrons. AES and XPS have so low sensitivity that lower quantizable concentration limits are several percentages, and are not suitable to quantify elements segregated in interfaces. The measurement must be conducted in vacuum, which is unsuitable for composition control of thin films.

Fluorescence analysis, in which fluorescent X-rays radiated when X-rays are irradiated to a sample are measured to give amounts of content elements, based on intensities of the fluorescent X-rays, can measure a total amount of fluorescent elements but cannot measure a distribution of the elements in the sample, which makes it difficult to evaluate concentrations of elements on a surface or an interface. In measuring nitrogen in an oxide film, it is difficult to separate nitrogen from oxygen, based on fluorescent X-rays.

Ellipsometry, which is an optical method and can make a non-destructive inspection, has a possibility that a concentration will be quantified based on reflective index changes of a film due to segregated elements. However, the ellipsometry cannot measure a concentration distribution, as cannot the fluorescence analysis, and it is difficult to evaluate element concentrations in a surface or an interface.

As described above, none of the conventional element concentration measuring methods are sufficient for quantifying a concentration of an element segregated on a surface and an interface. An element concentration measuring method which can measure with good precision readily in line a concentration of an element segregated on a surface and an interface.

SUMMARY OF THE INVENTION

An object of the present invention is to provide an element concentration measuring method and apparatus which can measure a concentration of an element on a surface and in an interface of a sample non-destructively readily with good precision.

Another object of the present invention is to provide a semiconductor fabrication method and apparatus having such element concentration measuring function.

The above-described objects can be achieved by an element concentration measuring method comprising: irradiating X-rays to a sample to be measured including at least one film formed on a substrate; measuring an interference oscillation curve of the X-rays reflected on the sample to be measured; and measuring a concentration of an element adhered on a surface of the sample to be measured and/or segregated in an interface of the film based on the interference oscillation curve. An element concentration is measured by the X-ray reflectance measurement, whereby a sample to be measured can be non-destructively inspected, and the method is applicable to inline process control. By the X-ray reflectance measurement a concentration of an element in a surface and an interface of a sample can be measured with good precision.

In the above-described element concentration measuring method it is preferable that the interference oscillation curve is fitted to an analysis formula expressing an X-ray reflectance to thereby determining a density of a region of the sample to be measured, where the element is adhered or is segregated; and a concentration of the element is computed based on the density. A density of a region of a sample to be measured, where an element is adhered or is segregated is thus determined, and, based on density, a concentration of the element can be quantified.

In the above-described element concentration measuring method it is preferable that at least one of a plurality of parameters for fitting the interference oscillation curve to the analysis formula, which has a small fluctuation among the sample to be measured is fixed. A parameter is thus fixed, whereby arbitrariness due to the fitting can be reduced, and accordingly an element concentration can be measured with high precision.

In the above-described element concentration measuring method it is preferable that the concentration of the element is computed based on an amplitude intensity of the interference oscillation curve. An amplitude intensity of the interference oscillation curve reflects a density of a region of a sample to be measured, where an element is adhered or segregated, and a concentration of the element on the sample surface and interface can be measured by analyzing an amplitude intensity of the interference oscillation curve which has been given by the measurement.

In the above-described element concentration measuring method it is preferable that a Fourier peak intensity is determined by Fourier-transforming the interference oscillation curve, and the concentration of the element is calculated based on the Fourier peak intensity. In quantifying an amplitude intensity of the interference oscillation curve, data of the interference oscillation curve is Fourier-transformed, and a Fourier peak intensity of a given curve reflects an amplitude intensity of the interference oscillation curve, so that the amplitude intensity of the interference oscillation curve can be measured without including arbitrariness. As a result, the element concentration measurement precision can be higher. The method of giving a Fourier peak intensity requires no skill in the data processing step, and the data processing takes a shorter time. Accordingly the element concentration measuring method is very effective for inline process control.

The above-described objects can be also achieved by an element concentration measuring apparatus comprising: X-ray source for irradiating X-rays at a prescribed angle to a sample to be measured including at least one film formed on a substrate; X-ray detector for detecting the X-rays reflected on the sample to be measured; and computer for computing a concentration of an element adhered on a surface of the sample to be measured and/or segregated in an interface of the film based on the interference oscillation curve. The element concentration measuring apparatus having this structure can non-destructively measure an element concentration with good precision. This apparatus is applicable to inline process control.

The above-described objects can be also achieved by a semiconductor device fabrication method comprising the steps of: forming on a semiconductor substrate a prescribed base structure including at least one film; and irradiating X-rays to the semiconductor substrate, measuring an interference oscillation curve of the X-rays reflected on the semiconductor substrate, and measuring, based on the interference oscillation curve, a concentration of an element adhered on the surface of the semiconductor substrate and/or segregated in an interface of the film. The element concentration measurement, which measures a concentration of an element adhered on the surface of a semiconductor substrate or segregated in the interface of the film by the X-ray reflectance measurement is applied to inline process control, whereby a concentration of an element adhered on the surface of the semiconductor substrate or segregated in the interface of the film can be correctly given in line and in a short time, whereby a measure result can be immediately fedback to processing conditions to reflect the subsequent processing of the semiconductor substrate. As a result, the semiconductor device fabrication can have high yields.

The above-described objects can be also achieved by a semiconductor device fabrication method comprising the steps of: forming a silicon oxide film on a silicon substrate; nitridizing the silicon substrate with the silicon oxide film formed on, and forming an interface layer containing nitrogen on an interface between the silicon substrate and the silicon oxide film; and irradiating X-rays to the substrate, measuring an interference oscillation curve of the X-rays reflected on the silicon Substrate with the silicon oxide film formed on, and measuring a nitrogen concentration in the interface layer, based on the interference oscillation curve. A concentration of nitrogen segregated in the interface between the silicon substrate and the silicon oxide film is controlled in line by the element concentration measuring method, whereby conditions for introducing nitrogen effectively to reduce impurity diffusion in the silicon substrate and an interface state can be immediately fedback for processing the following sample. As a result, the semiconductor device fabrication can have higher yields.

The above-described objects can be achieved by a semiconductor device fabrication apparatus comprising: a processing unit for subjecting a semiconductor substrate to a prescribed processing; and an element concentration measuring unit including an X-ray source for irradiating X-rays at a prescribed angle to the semiconductor substrate processed in the processing unit, X-ray detector for detecting the X-rays reflected on the semiconductor substrate, and computer for computing a concentration of an element adhered on a surface of the semiconductor substrate and/or segregated in an interface of the semiconductor substrate, based on an interference oscillation curve of the X-rays detected by the X-ray detector.

DETAILED DESCRIPTION OF THE INVENTION

A First Embodiment

The element concentration measuring method according to a first embodiment of the present invention will be explained with reference to FIGs. 1A–1F, 2 and 3.

Figure 2:
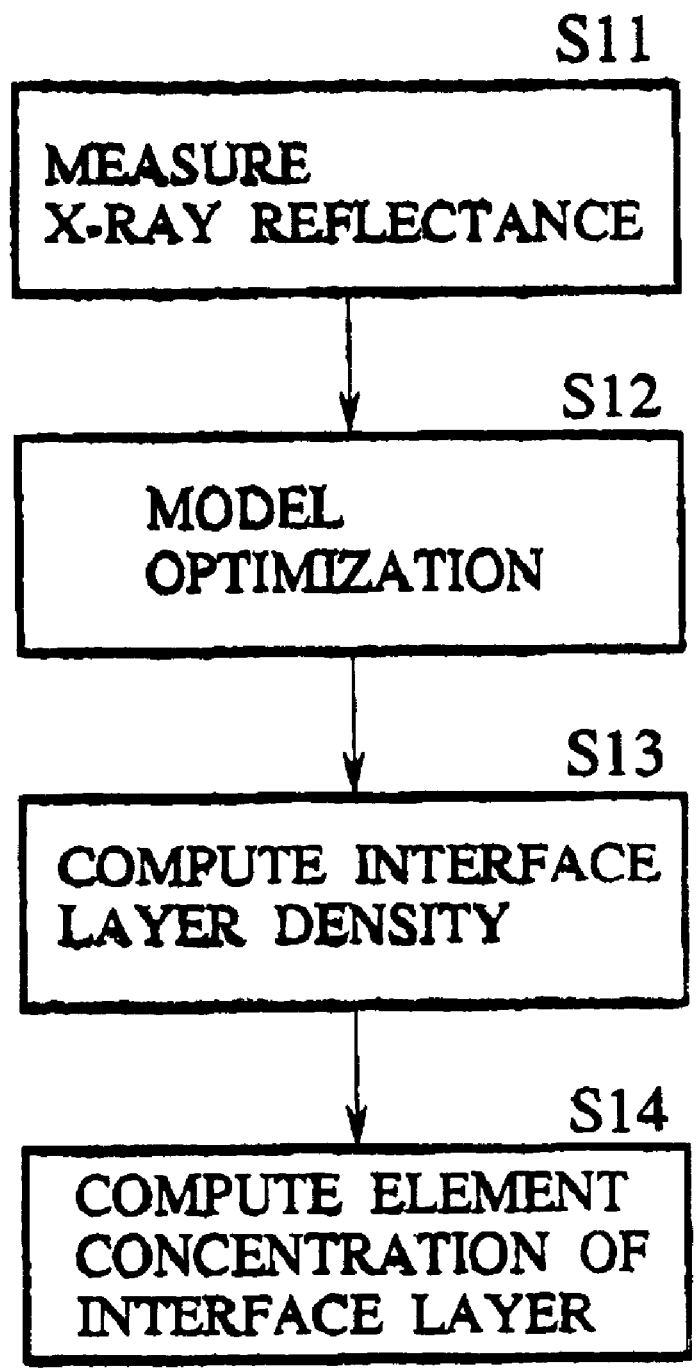
FIG. 2 is a diagrammatic flow chart of the Aliment concentration measuring method according to a first embodiment of the present invention.
Figure 3:
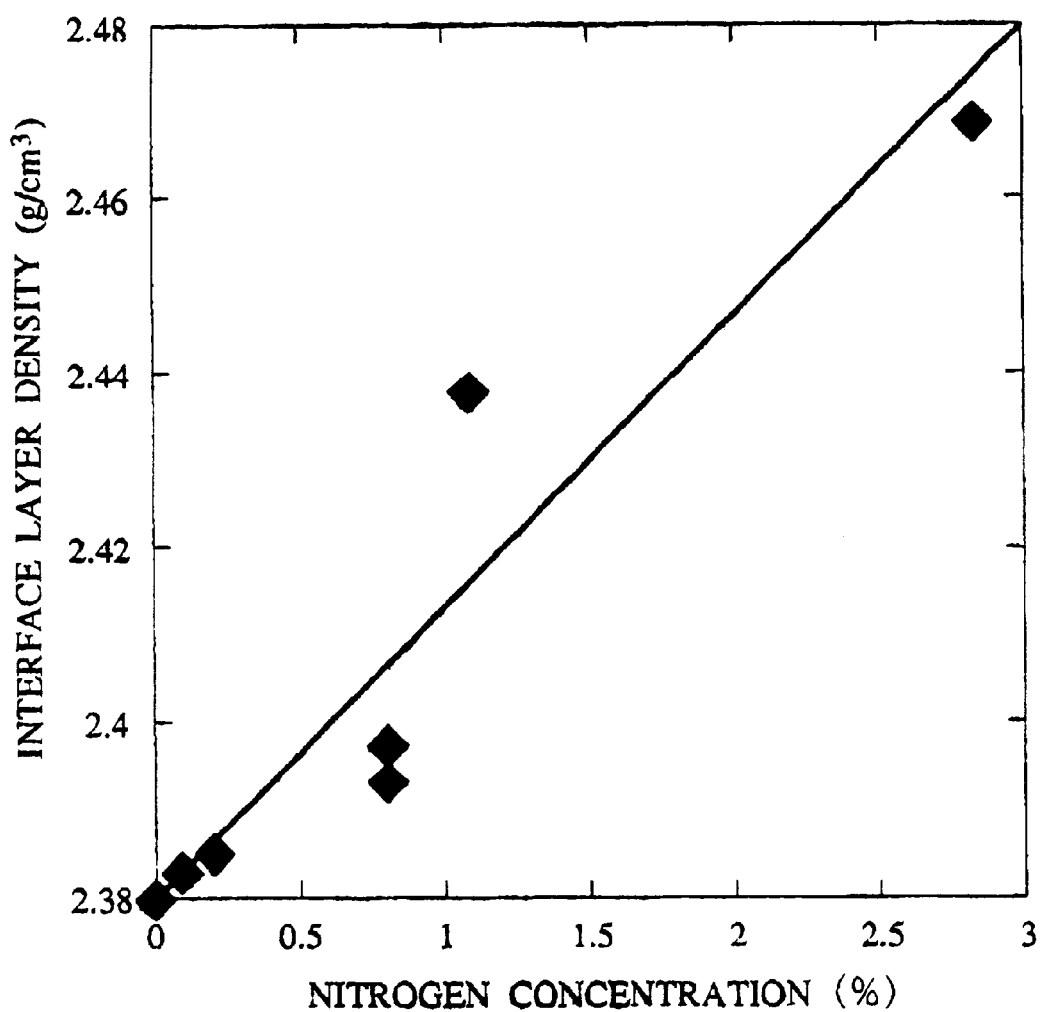
FIG. 3 is a graph of a calibration line for giving a nitrogen concentration in an interface layer, based on an interface layer density.

FIGs. 1A–1F are views explaining a principle of the element concentration measuring method according to the present embodiment. FIG. 2 is a flow chart of the element concentration measuring method according to the present embodiment, which diagrammatically shows the method. FIG. 3 is a graph of a calibration line for giving interface nitrogen concentration.

First, the principle of the element concentration measuring method according to the present embodiment will be explained with reference to FIGs. 1A–1F.

The element concentration measuring method according to the present embodiment quantifies a segregated element concentration, based on a result of the X-ray reflectance measurement.

As shown in FIG. .A, a sample to be measured with a film 6 formed on a substrate 2 is assumed, and the X-ray reflectance measurement is conducted on the sample.

When an X-ray is irradiated to the sample at an incident angle θ, the incident X-ray is reflected on the surface of the film 6, and on the interface between the film 6 and the substrate 2. When the general X-ray reflected on the sample is considered, the X-ray reflected on the surface of the film 6, and the X-ray reflected on the interface between the film 6 and the substrate 2 interfere with each other.

Figure 1A:
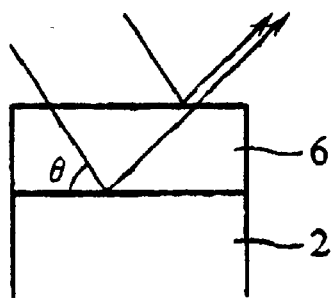
FIGs. 1A–1F are views explaining a principle of the element concentration measuring method according to the present invention.
Figure 1B:
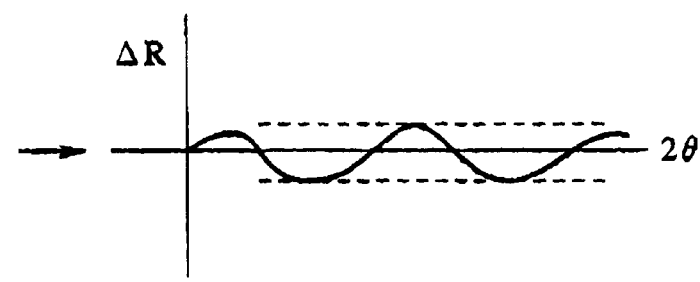

When the measurement is continued with an X-ray incident angle being gradually changed, an interference oscillating component of reflectances shown in FIG. 1B can be obtained.

Figure 1C:
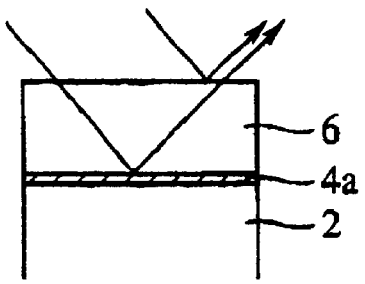

When a segregated layer 4a formed in the interface between the substrate 2 and the film 6 as shown in FIG. 1C is assumed, a region, such as the segregated layer 4a, where elements are integrated has a higher density. On the other hand, reflection of an X-ray takes place due to refractive index changes on the surface and on the interface, and a complex refractive index in an X-ray region is directly proportional to densities of substances. Accordingly, because of the segregated layer 4a, a higher reflectance occurs on the interface between the segregated layer 4a and the film 6, and an interference oscillating component given by the reflectances has a higher amplitude as shown in FIG. 1D.

Figure 1D:
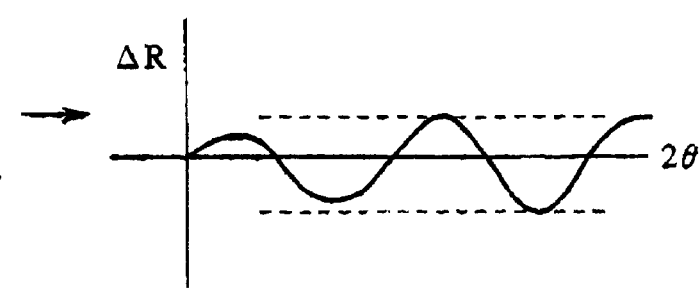
Figure 1E:
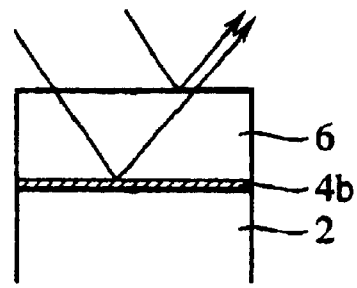
Figure 1F:
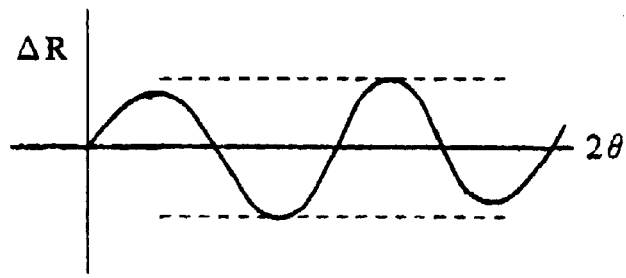

Similarly, when it is assumed that, as shown in FIG. 1E, a segregated layer 4b is present between a substrate 2 and a film 6, and the segregated layer 4b has a higher density than the segregated layer 4a, an interference oscillating component of given reflectances has a larger amplitude as shown in FIG. 1F than that in FIG. 1D.

Thus, because of the segregated layer 4 between the film 6 and the substrate 2, an interfered component of a given reflectance by the X-ray reflectance measurement changes depending on a density of the segregated layer 4. In other words, concentrations of segregated elements contained in the segregated layer 4 can be evaluated based on changes of the interfered component of the reflectance.

It is known that X-ray reflectance measurement can measure a film thickness and density of a multi-layer film with high precision. It is expected that concentrations of segregated elements in the segregated layer 4 can be quantified based on a thus-given density and film thickness of the segregated layer 4 for accurate element concentration measurement.

Then, a film thickness measuring method according to the present embodiment will be briefed with reference to FIG. 2.

First, X-rays are irradiated to the surface of a sample to be measured, changing an incident angle to measure X-ray reflectances, and an X-ray reflectance curve is given (Step S11). When the X-rays are Cu Ka rays (wavelength: 0.154 nm), it is preferable that an incident angle is changed in a range of 0–10°.

Then, the X-ray reflectance curve measured in the step S11 is fitted by model optimization (Step S12).

Subsequently, based on fitted model data, an interface layer density is determined (Step S13).

Then, based on a calibration curve prepared in advance, element concentrations are quantified via the calibration line, based on the given interface density (Step S14).

Then, the element concentration measuring method according to the present embodiment will be explained by means of a specific measurement example. In this example, a case which mainly comprises an interface layer containing nitrogen on the interface between a silicon substrate and a silicon oxide film formed on the silicon substrate will be explained, but the element concentration measuring method according to the present embodiment is not limited to this structure.

First, X-rays are irradiated to a sample to be measured, changing an incident angle to measure reflectances of the X-rays reflected on the sample, and an X-ray reflectance curve is given (Step S11). Because the X-rays are reflected on the surface and the interface of the sample to be measured, the measured X-ray reflectance curve contains an interference oscillating component.

Then, a structure model corresponding to the sample to be measured is assumed and is fitted to the X-ray reflectance curve given by the X-ray reflectance measurement (Step S12).

When the fitting is conducted, based on a structure model of, e.g., (a silicon oxide film/an interface layer/a silicon substrate), typical parameters are a density and a film thickness of the silicon oxide film, a density of the silicon substrate, a film thickness and a density of the interface layer, and roughnesses of the surface and the interface. Computation is repeated with these parameters changed to fit the structural model to the measured data to thereby evaluate values of these parameters.

The model optimization will be conducted in, e.g., the following process.

When a density of the silicon oxide film is represented by $\rho_1$; a complex refractive index, $n_1$; a film thickness, $t_1$; a density of the interface layer, $\rho_2$; a complex refractive index, $n_2$; a film thickness, $t_2$; a density of the silicon substrate, $\rho_3$, a complex refractive index, $n_3$; a complex refractive index of the atmosphere, $n_0$; a roughness of the surface of the silicon oxide film, $\sigma_1$; a roughness between the silicon oxide film and the interface layer, $\sigma_2$; and a roughness between the interface layer and the silicon substrate, $\sigma_3$, a model reflectance $R_{cal}$ is given by their function, based on Frenel's formula. Accordingly, when these parameters are given, a model reflectance $R_{cal}$ can be given by computation.

Here, a complex refractive index n is given by $$n=(1-\delta)+i\beta \quad (1)$$

where $$\delta=(r_e N_o/2\pi)\lambda^2 \rho(Z+f')/A$$

$$\beta=(r_e N_o/2\pi)\lambda^2 \rho f''/A$$

where $r_e$ represents a classical atomic radius; $N_o$, an Avogadro's constant; $\lambda$, an X-ray wavelength; $\rho$, a density (g/cm$^3$); Z, an atom number; A, a mass number; f', a dispersion compensation term; and f'', an absorption term.

Here, because the parameters except the density of a film can be given based on the value table, when a complex refractive index n is determined, densities $\rho$ is determined.

Then, $x^2$ expressed by the following expression is minimized by nonlinear least-squares method to determined the above-described parameters.

$$x^2=\Sigma[R_{meas}(\theta_i-R_{cal}(\theta_i,\rho_1\rho_2\rho_3 t_1 t_2 n_0 n_1 n_2 n_3 \sigma_1 \sigma_2 \sigma_3)]^2 \quad (2)$$

where $R_{meas}$ represents reflectance data given by measurement; and $\theta_i$, an incident angle; and i, 1 to n-number of data.

A complex refractive index n is thus given to thereby compute an interface layer density $\rho_2$.

The minimization can be conducted by, e.g., modified Marquardt method, simplex method or maximum entropy method.

Based on an interface layer density given by this model optimization, the following measurement of a nitrogen concentration is possible, but to actually practice the measurement it is necessary to give an interface layer density with very high precision, based on measured data. In the nonlinear least-squares fitting method, because of several parameters which are inter-related with one another, to give solutions having little deflection it is preferable that parameters which are considered to be invariable among samples are fixed at average values.

It is effective to fix, e.g., a density of the silicon oxide film $\rho_1$ a density of the silicon substrate $\rho_3$, roughnesses of the surface and the interface of a sample $\sigma_1$–$\sigma_3$ and a film thickness of the interface layer $t_2$. Typically it is preferable that a density of the silicon oxide film $\rho_1$ is 2.2–2.4, a film thickness of the interface layer $t_2$ is 0.8–1.5 nm, roughnesses of the surface and the interface $\rho_1$–$\sigma_3$ is 0–0.4 nm. Preferably these fixed parameters are adjusted suitably in accordance with preparation conditions, etc. of samples.

An interface layer density $\rho_2$ optimized by the model optimization is given (Step S13).

Subsequently, based on the given interface layer density by the model optimization, a nitrogen concentration in the interface layer is given (Step S14). The nitrogen concentration in the interface layer can be given directly based on an interface density by the use of, e.g., a calibration line measured beforehand.

The calibration line can be obtained by measuring in advance nitrogen concentrations in the interface layers by, e.g., SIMS analysis. For example, a plurality of samples having different nitrogen concentration in the interface layer are prepared, and interface layer densities of the samples are measured by the above-described X-ray reflectance measurement, nitrogen concentrations in the interface layers are measured by SIMS analysis, and their relationships are graphed.

FIG. 3 shows one example of relationships between the interface layer densities and the nitrogen concentrations in the interface layers thus given. In FIG. 3, ♦ indicates results measured by SIMS analysis, and the data were approximated to the straight line.

In the calibration line shown in FIG. 3, the interface layer densities and the nitrogen concentrations in the interface layers are substantially proportional to each other. This relationship between the interface layer densities and the nitrogen concentrations in the interface layers is approximated by the linear line, based on the following model.

The model optimization of data given by the X-ray reflectance measurement shows that when nitrogen is introduced between the silicon substrate and the silicon oxide film, the introduction of the nitrogen resulted in higher densities of the interface layer of an about 1 nm-thick. This is due to that the nitrogen is segregated in the interface between the silicon substrate and the silicon oxide film with a result that reflectances of X-rays on the interface are higher, and interference oscillations of interference with the X-rays reflected on the interface are stronger. Based on the measurement result by the XPS, it is known that the nitrogen in the interface region is combined with the Si in the form of $Si_3N_4$. The density of the silicon nitride ($Si_3N_4$) is 2.9 g/cm$^3$ which is higher in comparison with 2.4 g/cm$^3$ which is the density of silicon oxide film. This is consistent with the above result.

Appreciation by X-ray CTR measurement found that the introduced nitrogen does not break the crystal phase of the silicon oxide film, and it is considered that density changes of the interface layer are directly proportional to nitrogen concentration changes.

Then, when it is assumed that nitrogen is present simply in the form of $Si_3N_4$, an interface layer density $\rho$ is expressed $$\rho=\rho_{SiO_2}+x\rho_{Si_3N_4} \quad (3)$$

where a density of the silicon oxide film is represented by $\rho_{SiO_1}$; a density of the silicon nitride film, $\rho_{Si_3N_4}$; and a ratio of presence of the silicon nitride film, x.

Accordingly, a ratio of presence of the silicon nitride film x can be given by $$x=(\rho-\rho_{SiO_1})/\rho_{Si_3N_4} \quad (4)$$

As apparent in formula (4), a ratio of presence of the silicon nitride film x indicative of a nitrogen concentration in the interface layer is proportional to an interface layer density $\rho$, which endorses the result of the SIMS analysis shown in FIG. 3.

Thus, a calibration line as shown in FIG. 3 is prepared in advance, an interface layer density of an arbitrary sample is given by the X-ray reflectance measurement, whereby a nitrogen concentration in the interface layer can be measured based on the interface density trough the calibration line.

For example, when an interface layer density is 2.44, based on the model optimization of the X-ray reflectance measurement, the nitrogen concentration in the interface layer can be estimated to be about 1.8%, based on the calibration line of FIG. 3.

As described above, according to the present embodiment, a concentration of an element segregated in an interface layer, based on interference oscillation data of reflected X-rays given by the X-ray reflectance measurement, whereby a concentration of the element in the interface layer can be non-destructively measured with high precision.

In the present embodiment, a nitrogen concentration in an interface layer containing nitrogen formed on the interface between a silicon oxide film and a silicon substrate, but the same measurement can be conducted on other material systems.

In the above-described example of (a silicon oxide film/an interface layer/a silicon substrate), the calibration curve can be approximated by the linear function, but it is understood that a shape of the calibration curve changes in accordance with a structure and a reaction system of a sample. Accordingly, the above-described proportional relationship is not always given.

In short, it suffices that a set relationship is given between interface layer densities and interface impurity concentrations, and a suitable model is used in accordance with a sample to prepare a calibration curve suitable for the model. In this case, the calibration curve can be given in the same way as in the present embodiment.

The X-ray reflectance measurement can measure a concentration and a film thickness of a segregated layer formed not only on a film interface but also on a sample surface. For example, when water staying on the surface of a sample is measured, the element concentration measuring method according to the present embodiment can be applied.

A Second Embodiment

The element concentration measuring method according to a second embodiment of the present invention will be explained with reference to FIGS. 4 to 10.

Figure 4:
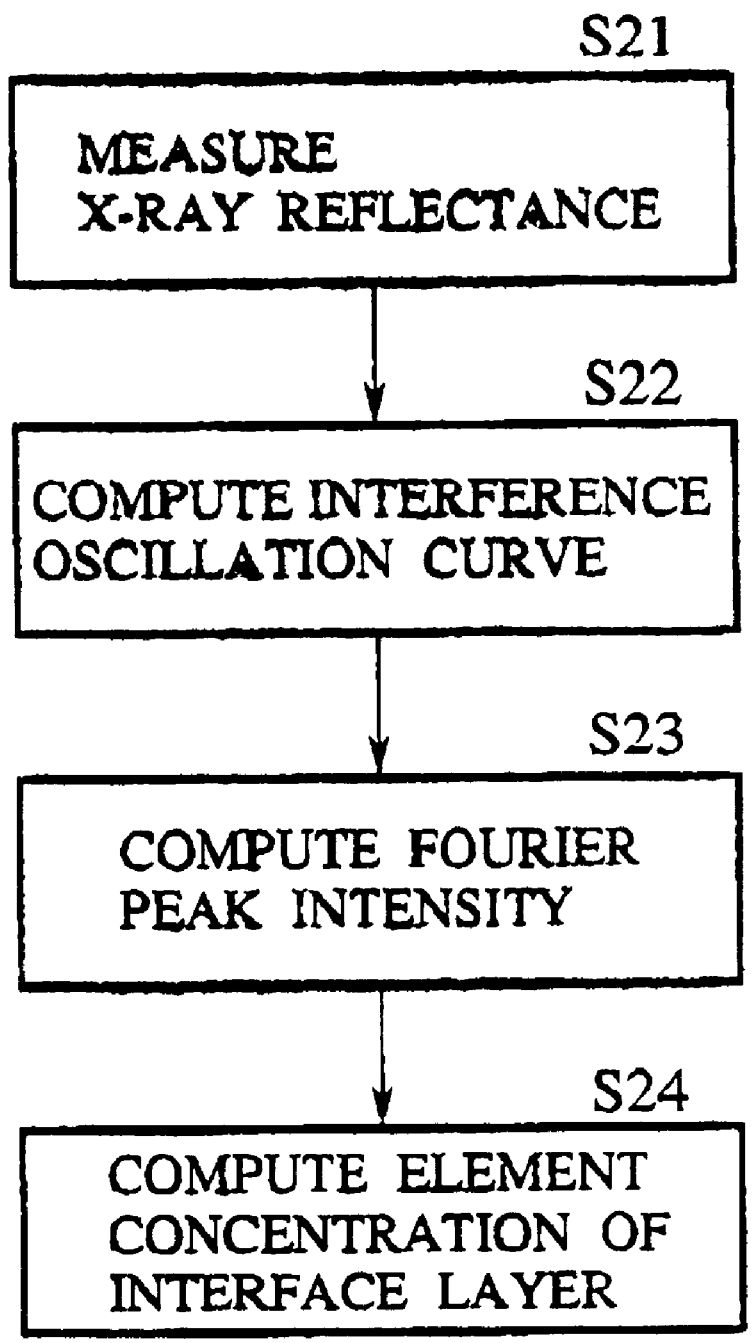
FIG. 4 is a diagrammatic flow chart of the element concentration measuring method according to a second embodiment of the present invention.
Figure 5A:
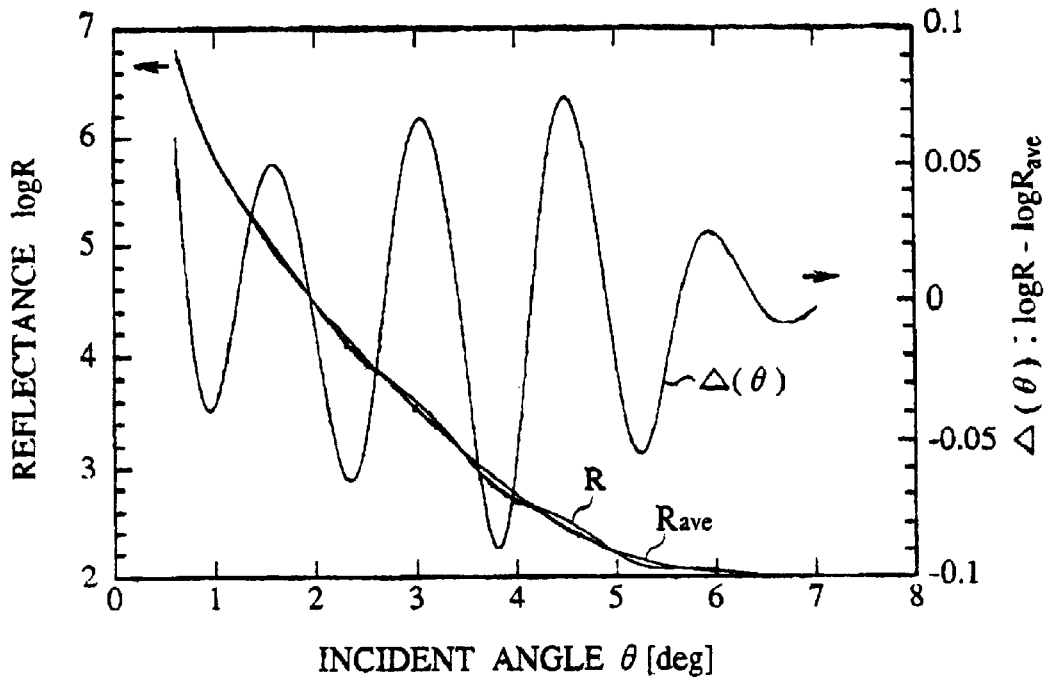
FIGS. 5A and 5B are graphs of computed data given by the element concentration measuring method according to the second embodiment of the present embodiment.
Figure 5B:
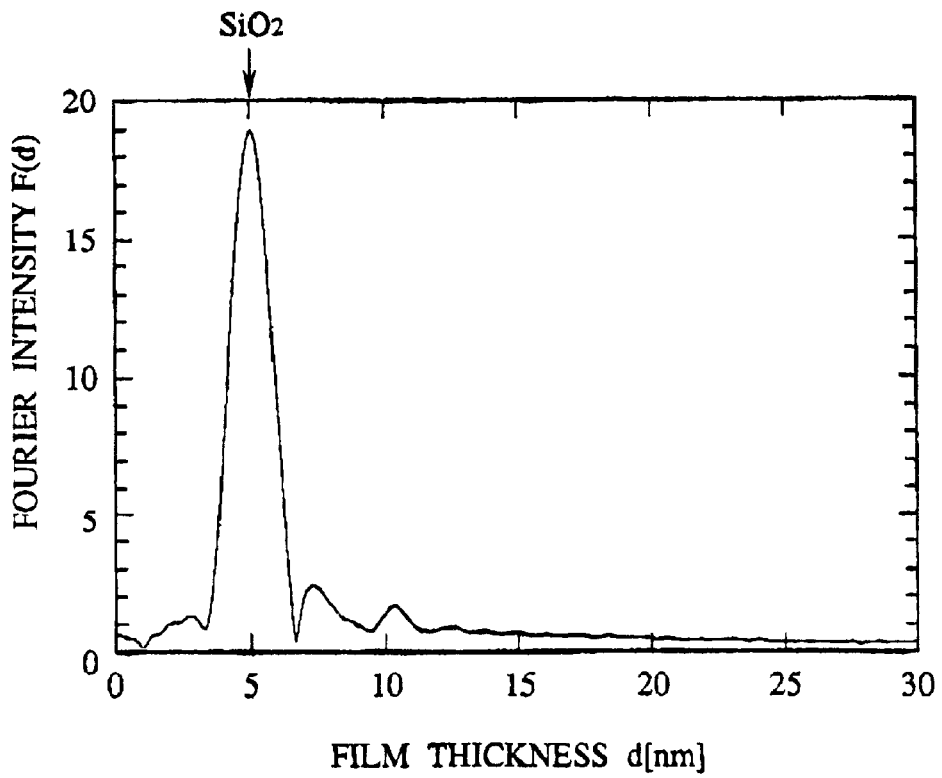
Figure 6:
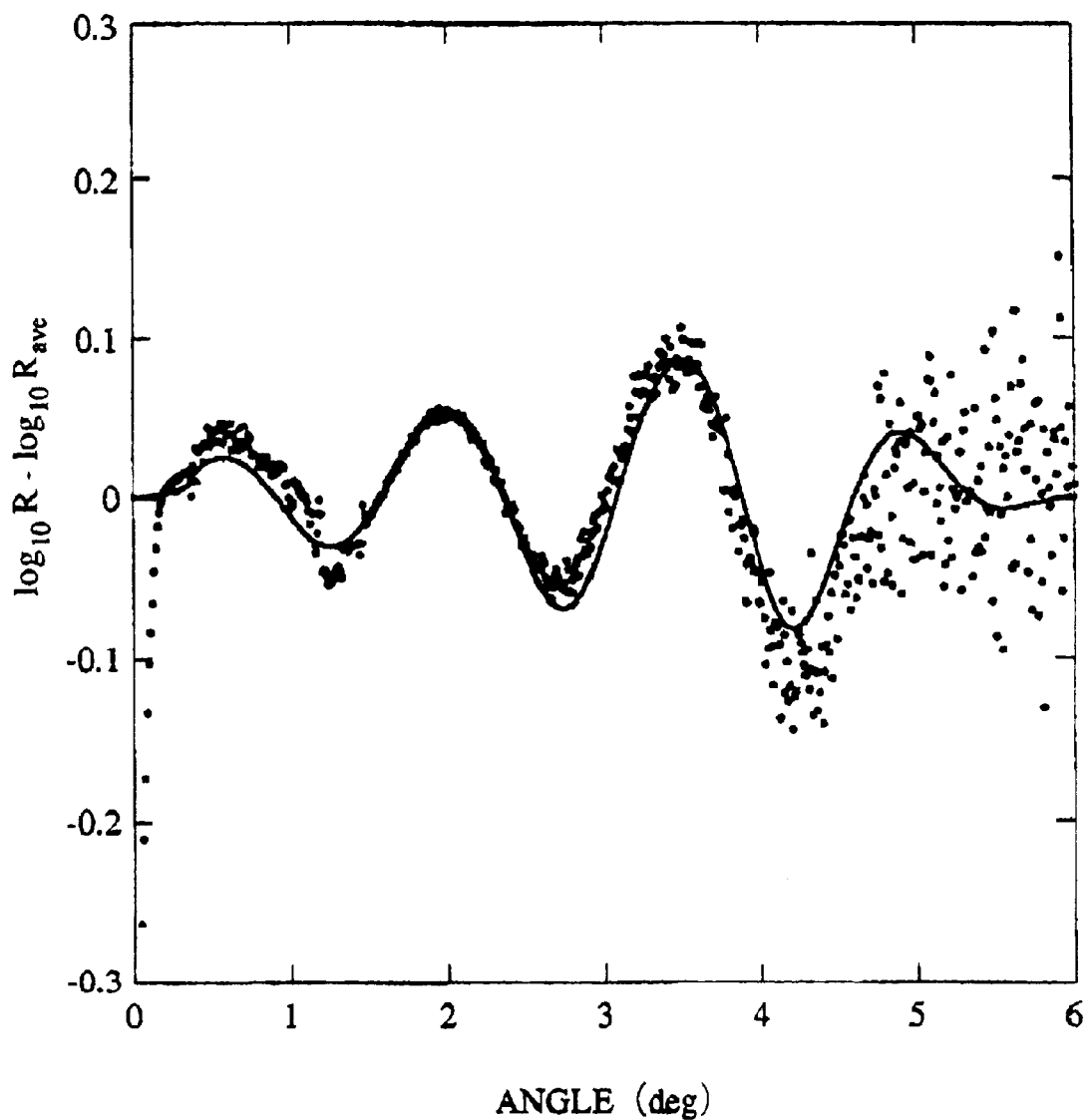
FIG. 6 is a graph of a result of interference oscillation component extracted from an X-ray reflectance curve (Part 1).
Figure 7:
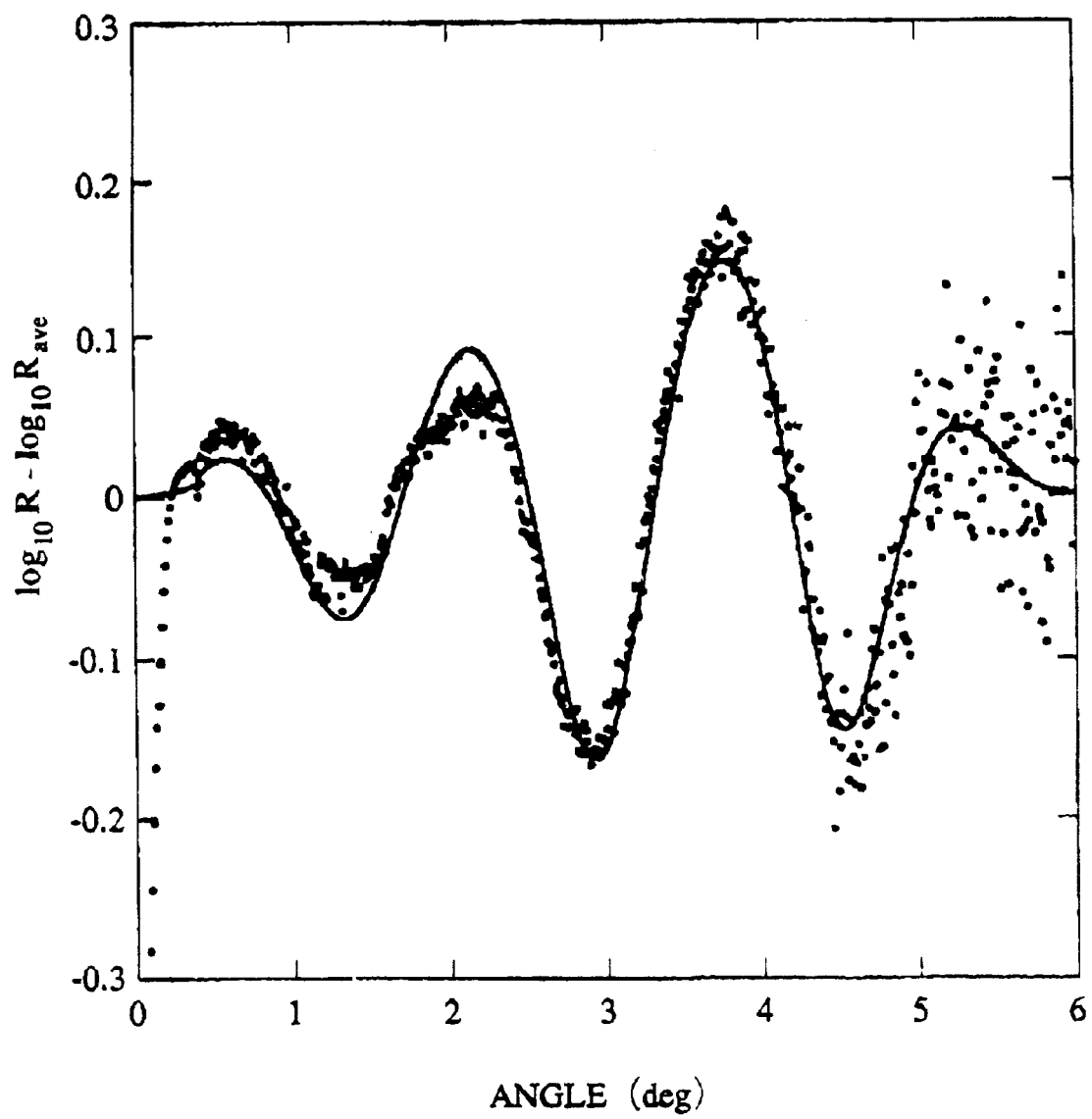
FIG. 7 is a graph of a result of interference oscillation component extracted from an X-ray reflectance curve (Part 2).
Figure 8:
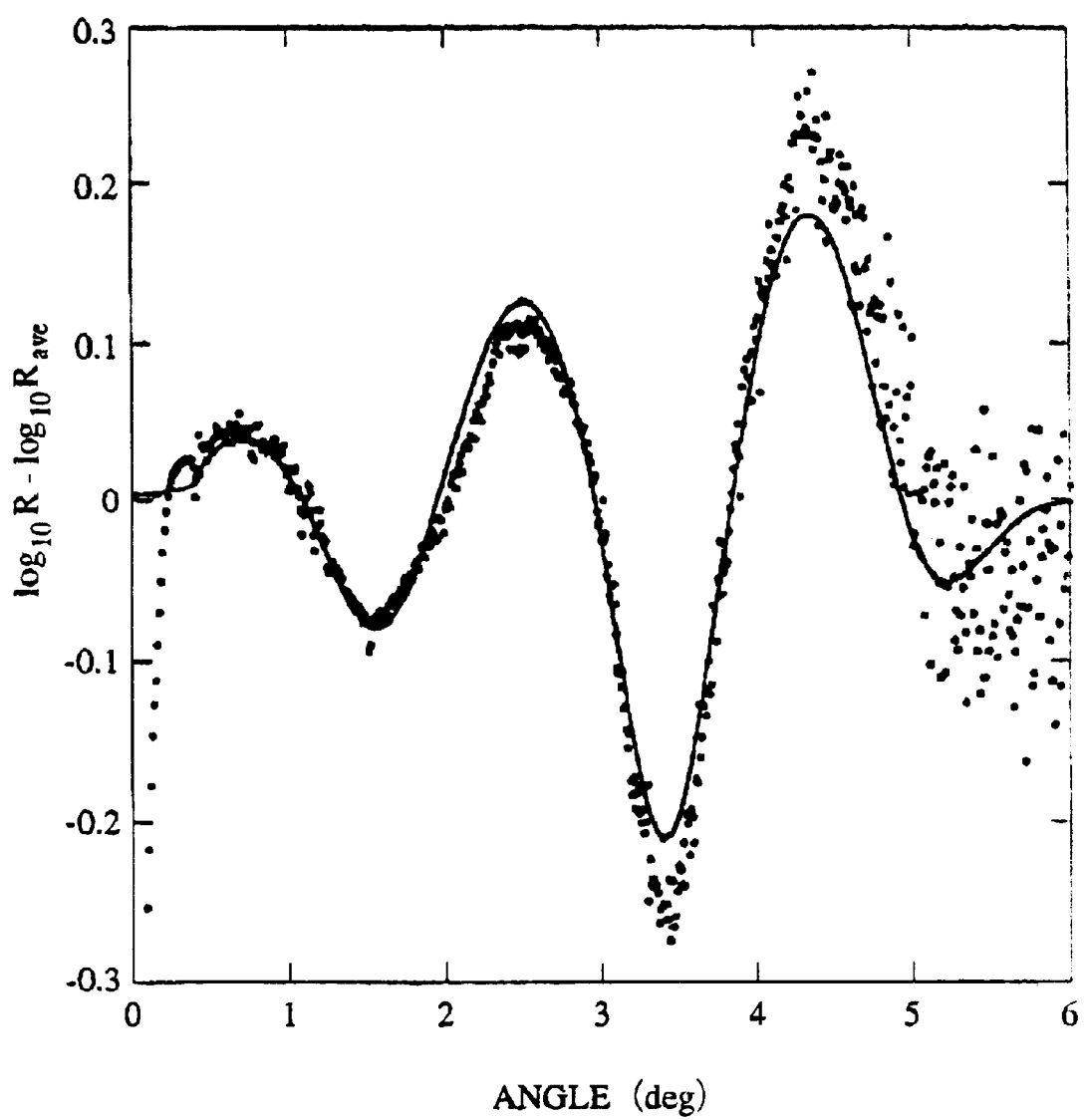
FIG. 8 is a graph of a result of interference oscillation component extracted from an X-ray reflectance curve (Part 3).
Figure 9:
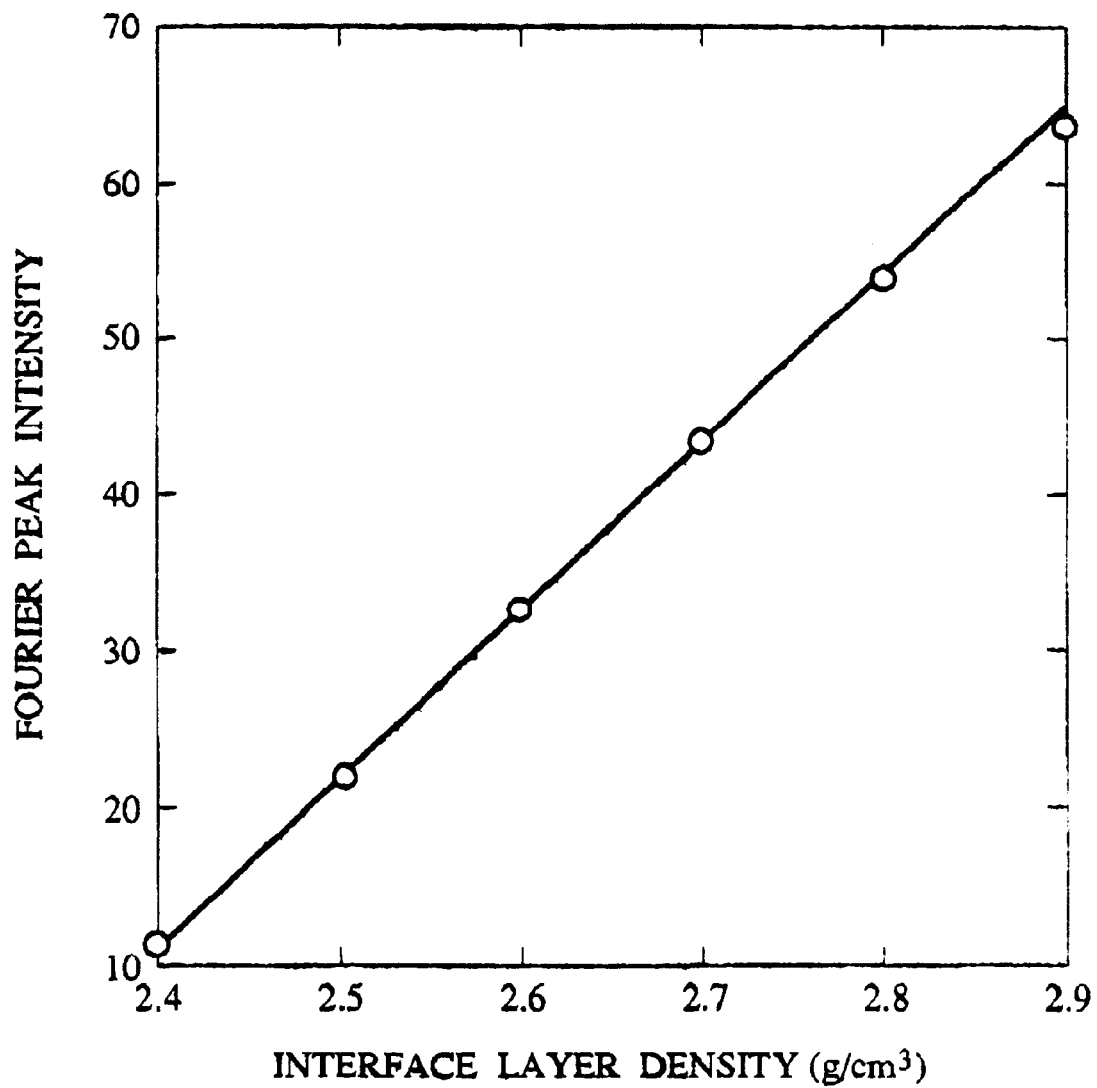
FIG. 9 is a graph of relationship between the interface layer density and the Fourier peak intensity given by simulation.
Figure 10:
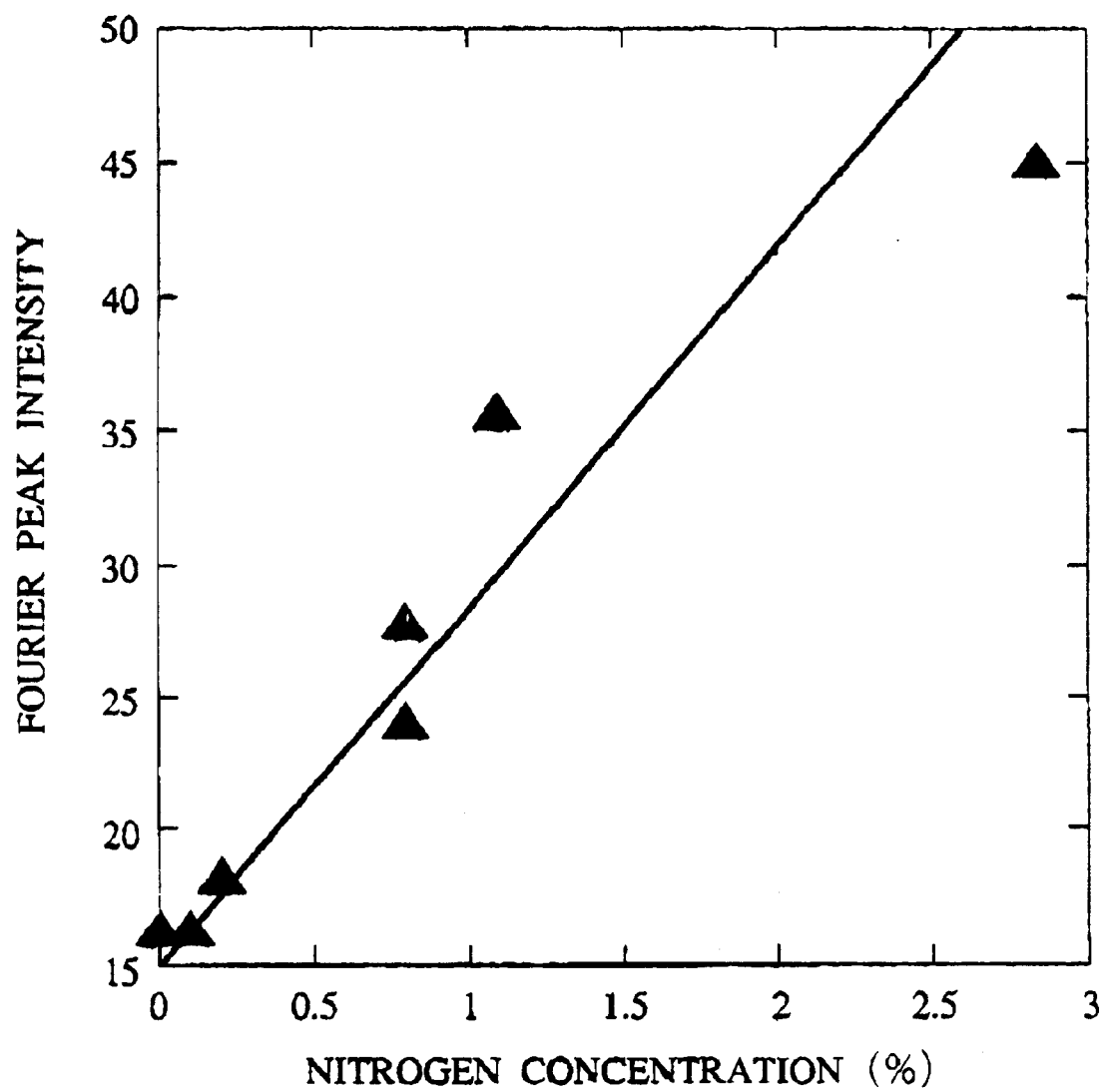
FIG. 10 is a graph of a calibration line for giving a nitrogen concentration in an interface layer, based on a Fourier peak intensity.

FIG. 4 is a flow chart of the element concentration measuring method according to the present embodiment. FIGs. 5A and 5B are graphs of computed data by the element concentration measuring method according to the present embodiment. FIGS. 6 to 8 are graphs of results of extraction of interference oscillating components from x-ray reflectance curves. FIG. 9 is a graph of a result of relationship between interface layer densities and Fourier peak intensities given by simulation. FIG. 10 is a graph of a calibration line for giving a nitrogen concentration in the interface layer, based on a Fourier peak intensity.

In the first embodiment, reflectance data given by the X-ray reflectance measurement were fitted by the model optimization to thereby quantify an element concentration of the interface layer. This model optimization needs some skill and time unsuitably to be applied to inline process control for simple appreciation. Then, the present embodiment shows the element concentration measuring method for more readily measuring an element concentration in a segregated layer.

First, a film thickness measuring method according to the present embodiment will be briefed with reference to FIG. 4.

First, in the same way as the element concentration measuring method according to the first embodiment, X-rays are irradiated to the surface of a sample to be measured, changing an incident angle to give an X-ray reflectance curve R (Step S21).

Then, based on the X-ray reflectance curve R measured in Step S21, an interference oscillation curve $\Delta(x)$ is given (Step S22).

Subsequently, the thus-given interference oscillation curve $\Delta(x)$ is Fourier-transformed to give a peak intensity of a Fourier coefficient F(d) (Step S23).

Then, by using a calibration curve prepared in advance, an element concentration is quantified based on the give Fourier peak intensity through the calibration curve (Step S24).

Next, the element concentration measuring method according to the present embodiment will be detailed by means of an example of the measurement.

In the same way as the element concentration measuring method according to the first embodiment, X-rays are irradiated to the surf ace of a sample to be measured, changing an incident angle to measure X-ray reflectances and give an X-ray reflectance curve R (Step S21). As exemplified in FIG. 5A, measured data R obtained by the X-ray reflectance measurement contain a general reflected component (an average reflectance $R_{ave}$) from the substrate, and to make the measurement accurate it is preferable that the general reflected component from the substrate is removed.

A general reflected component from the substrate can be evaluated by the method described in, e.g., the specification of Japanese Patent Application No. 142665/1996.

For example, the analysis formula described in the specification of Japanese Patent Application No. 142665/1988

$$R_{ave}=I_0(\theta-\theta_0)^{-4}\cdot\exp[-(4\pi\sigma/\lambda\cdot\sin\theta)^2]+B_0$$

can be used.

In the analysis formula, $1a$ represents an intensity; $\theta$, an incident angle of X-ray; $\theta_0$ represents an origin compensation value of $\theta$; $\sigma$, a mean square value of roughness of a sample surface; $\lambda$, a wavelength of X-ray; and $B_0$, a background constant.

The thus given average reflectance $R_{ave}$ is subtracted from the measured data R, whereby an interference oscillation curve $\Delta(\theta)$ can be extracted from the measured data R.

FIGS. 6 to 8 show graphs of results of thus-extracted interference oscillation components of samples prepared under various conditions. FIG. 6 shows a graph of a result obtained on a sample with a 5 nm-thick silicon oxide film alone formed on. FIG. 7 is a graph of a result obtained on a sample which is nitrified at 800° C. after a 5 nm-thick silicon oxide film is formed. FIG. 8 is a graph of a result obtained on a sample which is nitridized at 900° C. after a 4 nm-thick silicon oxide film is formed.

Then, the thus-given interference oscillation curves $\Delta(\theta)$ are changed to interference oscillation curves $\Delta(x)$ by change of variables (Step S22).

Subsequently the thus-given interference oscillation curves $\Delta(x)$ are Fourier-transformed. When the interference oscillation curve $\Delta(x)$ shown in FIG. 5A, for example, is Fourier-transformed, the graph shown in FIG. 5B is given. The method for giving the graph shown in FIG. 5B from an x-ray reflectance curve R is detailed in, e.g., the specification of Japanese Patent Application No. 142665/1996 filed by the applicant of the present application.

The element concentration measuring method according to the present embodiment uses Fourier transformation as means for directly corresponding an amplitude of an interference oscillation to a nitrogen concentration.

That is, as described in the first embodiment, a change in an interface layer density is reflected in an amplitude of an interference oscillation. Accordingly, if an amplitude of an interference oscillation and a nitrogen concentration can be directly corresponded to each other, it is expected that it will facilitate the element concentration measurement. On the other hand, in considering that an amplitude of an oscillation is given based on an interference amplitude, it is a problem how and at what incident angle an amplitude of an interference oscillation is determined because an interference oscillation has a period of an oscillation thereof closely related with a film thickness. This is because Fourier transformation is effective to this case.

Then, a Fourier peak intensity is read from the thus-given graph (Step S23). A peak position of this graph indicates a film thickness of the silicon oxide film. On the other hand, a peak intensity of a Fourier coefficient F(d) indicates a value related to an amplitude of an interference oscillation curve. Accordingly, an interface layer density can be given by analyzing a Fourier peak intensity.

Then, to compute an interface density based on a Fourier peak intensity it is necessary to know what relationships these parameters have with one another. Then, a model of the (silicon oxide film/an interface layer/silicon substrate) structure is assumed, and a relationship between a Fourier peak intensity and an interface layer density was simulated.

FIG. 9 is a graph of a result given by simulating a relationship of interface layer densities and Fourier peak intensities when the silicon oxide film has a 5 nm-thick and a 2.3 g/cm$^3$ and the interface layer has a 0.5 nm-thick.

As shown, it is found that Fourier peak intensities and interface layer densities have a proportional relationship.

Thus, without computing an interface layer density by the model optimization of the element concentration measuring method according to the first embodiment, a value of the interface density can be estimated based on a Fourier peak intensity. That is, an element concentration in the interface layer can be computed directly based on a Fourier peak intensity without using an interface layer density.

A peak intensity given by Fourier transformation of interference oscillation data has no arbitrariness the model optimization has, and can measure a peak intensity more readily with high precision.

Then, a nitrogen concentration in the interface layer is given based on the Fourier peak intensity given by Fourier transformation of the interference oscillation curve $\Delta(x)$ (Step S24). The nitrogen concentration in the interface layer can be given directly based on an interface layer density by the use of, e.g., a calibration curve prepared in advance.

The calibration curve can be given by measuring beforehand the nitrogen concentrations in the interface layers by, e.g., SIMS analysis. For example, a plurality of samples having different nitrogen concentration in the interface layer from each other are prepared, Fourier peak intensities and nitrogen concentrations in the interface layers are measured respectively by the above-described X-ray reflectance measurement and the SIMS analysis, and their relationships are graphed.

FIG. 10 is one example of relationships between the thus-given interface layer densities and the nitrogen concentrations in the interface layers. In FIG. 10, ♦ indicates a measured result by the SIMS analysis, and the solid line indicates a calibration line given by approximating measured data by the SIMS analysis.

The calibration line shown in FIG. 10 is prepared in advance, a Fourier peak intensity of an arbitrary sample is measured by the X-ray reflectance measurement, and the nitrogen concentration in the interface layer is measured based on a Fourier peck intensity trough the calibration line.

For example, when a Fourier peak intensity is given based on an interferers oscillation curve $\Delta(x)$, the nitrogen concentration in the interface layer can be estimated to be about 1.5%, based on the calibration line in FIG. 10.

A measurement precision of the computation based on the calibration line Is within ±0.2–0.3% when the nitrogen concentration is about 1%. A very high precision can be attained.

As described above, according to the present embodiment, a Fourier peak intensity given by Fourier transformation of interference oscillation can be related directly with a concentration of an element in the interface layer, so that a concentration of a segregated element can be readily quantified based on a Fourier peak intensity given by Fourier transformation of interference oscillation given by the X-ray reflectance measurement.

The element concentration measuring method according to the present embodiment does not require skilled technique required in the data processing step of the element concentration measuring method according to the first embodiment, which makes the element concentration measuring method according to the present embodiment easily applicable to inline process check. In other words, a graph given by the X-ray reflectance measurement is simply Fourier-transformed to evaluate a concentration of a segregated element. Accordingly, operators do not need professional knowledge, and the computing time can be short.

In the present embodiment, the nitrogen concentration is quantified on an interface layer containing nitrogen formed on the interface between a silicon oxide film and a silicon substrate is measured, but the quantification can be conducted on other materials. Element concentrations can be quantified in the same way on surface segregated layers.

A Third Embodiment

The element concentration measuring apparatus and a semiconductor fabrication apparatus according to a third embodiment of the present invention will be explained with reference to FIGS. 11 and 12.

Figure 11:
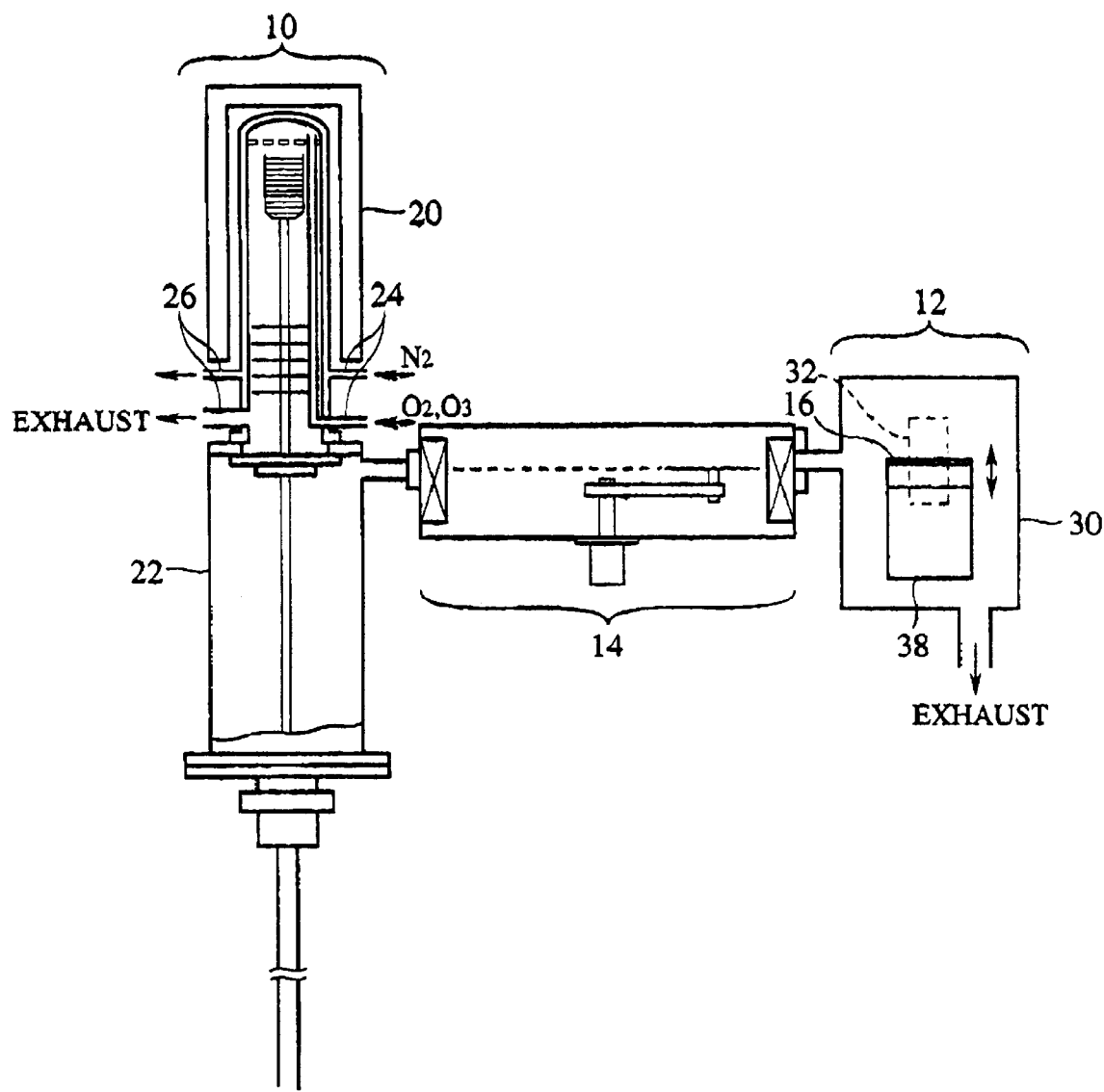
FIG. 11 is a schematic side view of the semiconductor device fabrication apparatus according to a third embodiment of the present invention.
Figure 12:
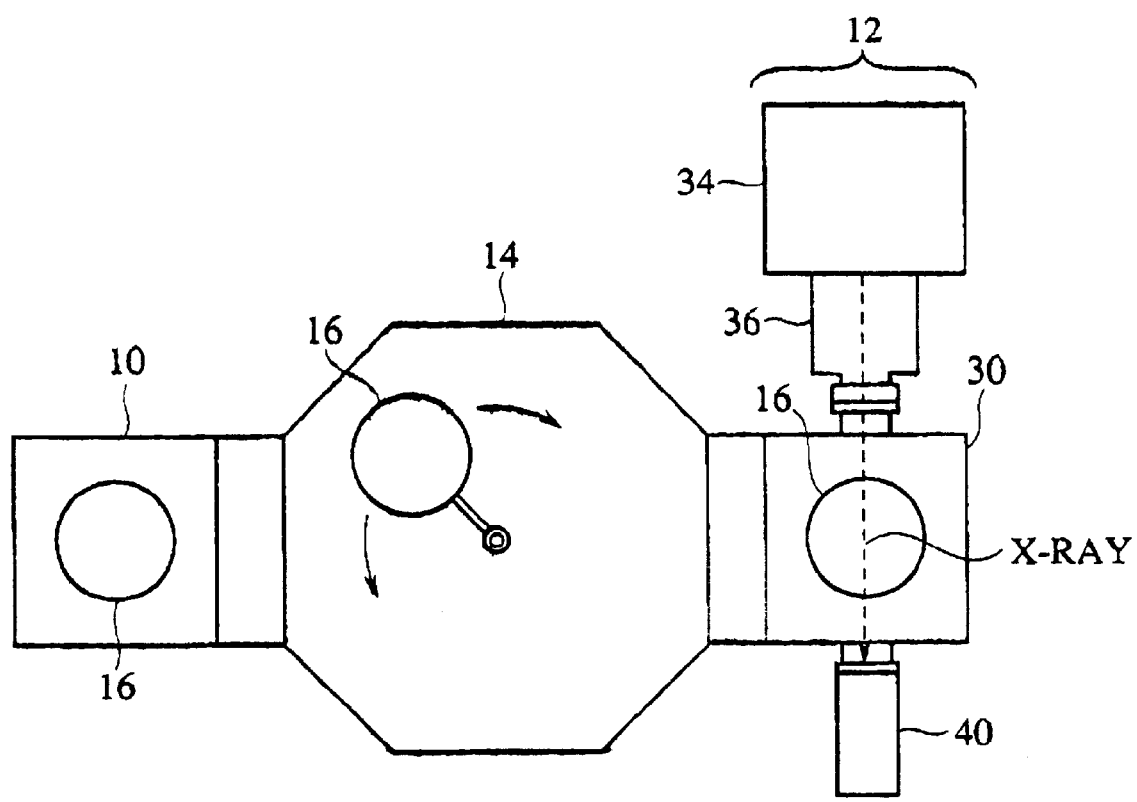
FIG. 12 is a schematic top view of the semiconductor device fabrication apparatus according to a third embodiment of the present invention.

FIG. 11 is a diagrammatical side view of the semiconductor fabrication apparatus according to the present embodiment. FIG. 12 is a diagrammatical top view of the semiconductor fabrication apparatus according to the present embodiment.

The present embodiment shows an element concentration measuring apparatus and a semiconductor device fabrication apparatus which can use the element concentration measuring method according to the first and the second embodiments in inline control.

The semiconductor device fabrication apparatus according to the present embodiment comprises a processing unit 10 for subjecting semiconductor wafers 16 to prescribed semiconductor fabrication processing, an element concentration measuring apparatus 12 for measuring an element concentration in the interface layer by the X-ray reflectance measurement, and a transfer chamber 14 for transferring the semiconductor wafers 16 to be measured from the processing unit 10 to the element concentration measuring apparatus 12.

The processing unit 10 comprises an oxidation furnace 20 for processing the semiconductor wafers 16, and wafer transfer means 22 for loading the semiconductor wafers 16 to be processed in the oxidation furnace 20. The oxidation furnace 20 has a gas feed port 24 and an exhaust port 26, so that processing using prescribed gases can be conducted in the oxidation furnace 20. In the semiconductor device fabrication apparatus shown in FIG. 11 $N_2$ gas, $O_2$ gas and $O_3$ gas can be fed, and processing using these gases can be conducted.

The semiconductor device fabrication apparatus shown in FIG. 11 comprises the processing unit 10 including a heat treatment apparatus for oxidation, nitridation and other heat-treatment of semiconductor wafers 16 but may comprise other processing apparatuses requiring the element concentration measurement after processing.

The wafer transfer means 22 is connected to the transfer chamber 14 so that the semiconductor wafers 16 processed in the oxidation furnace 20 are transferred to the element concentration measuring apparatus 12, or from the element concentration measuring apparatus 12 to the processing unit 10.

The transfer chamber 14 is connected to a measurement chamber 30 of the element concentration measuring apparatus 12 so that the semiconductor wafers 16 processed in the processing unit 10 are carried to the measurement chamber 30 through the transfer chamber 14.

The measurement chamber 30 has a beryllium window 32 in the outside wall so that X-rays radiated by a rotor X-ray source 34 are introduced into the measurement chamber 30 through a Ge (111) monochromator 36.

A stage 38 for a semiconductor wafer 16 to be mounted on is disposed in the measurement chamber 30. The stage 38 includes stage moving means (not shown) for moving the stage in a Z-axial direction, an $R^x$-axial direction, an $R_y$-axial direction, $\phi$-axial direction, an X-axial direction and $\theta$-axial direction so that X-rays are irradiated to the semiconductor wafer 16 at prescribed incident angles.

The measurement chamber 30 includes an X-ray detector 40 on the side opposed to the X-ray source 34 so that X-rays reflected on the semiconductor wafer 16 on the stage 38 can be detected.

The element concentration measuring apparatus 12 is connected to control means (not shown) for controlling the element concentration measuring apparatus when the element concentration measurement is conducted, computing means (not shown) for measuring an element concentration, based on measured data, and other means.

Then, the element concentration measuring method using the semiconductor fabrication apparatus according to the present embodiment will be explained.

Prescribed wafer processing is conducted in the processing unit 10. For example, a silicon substrate is oxidized in the oxidation furnace 20 to form a silicon oxide film, and then prescribed nitridation is conducted to form a substrate-to-be-measured having a nitrogen content interface layer on the interface between the silicon substrate and the silicon oxide film.

Then, the substrate-to-be-measured is taken out of the oxidation furnace 20 by the wafer transfer means 22 to transfer the substrate-to-be-measured to the element concentration measuring apparatus 12 via the transfer chamber 14. The substrate-to-be-measured transferred to the element concentration measuring apparatus 12 is mounted on the stage 38 in the measurement chamber 30.

Subsequently, the X-ray reflectance measurement is conducted on the substrate-to-be-measured on the stage 38. For example, X-rays from the X-ray source 34 are irradiated to the substrate-to-be-measured while the stage 38 is moved by the control means to gradually change incident angles of the X-rays, and intensities of the X-rays reflected on the sample-to-be-measured are detected by the X-ray detector 40.

Then, measured data given by the X-ray reflectance measurement are analyzed by the computing means, and the nitrogen concentration in the interface layer containing nitrogen is quantified. For the nitrogen concentration quantification the element concentration measuring method according to, e.g., the second embodiment is used.

According to the element concentration measuring method according to the second embodiment, interference oscillation data given by the X-ray reflectance measurement is Fourier-transformed to compute the nitrogen concentration, based on a Fourier peak intensity. Accordingly, as described above, the computation of the nitrogen concentration requires no skill, which makes it possible operators to readily compute in line the nitrogen concentration. No repeated computation, such as the model optimization, is required, which makes it possible to compute a concentration in a short time.

As described above, according to the present embodiment, the nitrogen concentration in an interface layer can be readily computed in line, and when it is found that the computed nitrogen concentration is not within a prescribed allowance range, operators can immediately feedback the data to processing conditions for the following wafer processing.

In the present embodiment, the semiconductor fabrication apparatus includes the element concentration measuring apparatus and the processing apparatus combined with each other, but they are not essentially combined.

What is claimed is:

1. An element concentration measuring method comprising:

irradiating X-rays to a sample to be measured including at least one film formed on a substrate;

measuring an interference oscillation curve of the X-rays reflected on the sample to be measured; and measuring a concentration of an element adhered on a surface of the sample to be measured and/or segregated in an interface of the film based on the interference oscillation curve.

2. An element concentration measuring method according to claim 1, wherein the interference oscillation curve is fitted to an analysis formula expressing an X-ray reflectance to thereby determining a density of a region of the sample to be measured, where the element is adhered or is segregated; and a concentration of the element is computed based on the density.

3. An element concentration measuring method according to claim 2, wherein at least one of a plurality of parameters for fitting the interference oscillation curve to the analysis formula, which has a small fluctuation among the sample to be measured is fixed.

4. An element concentration measuring method according to claim 1, wherein the concentration of the element is computed based on an amplitude intensity of the interference oscillation curve.

5. An element concentration measuring method according to claim 4, wherein a Fourier peak intensity is determined by Fourier-transforming the interference oscillation curve, and the concentration of the element is calculated based on the Fourier peak intensity.

6. A semiconductor device fabrication method comprising the steps of:

forming on a semiconductor substrate a prescribed base structure including at least one film; and irradiating X-rays to the semiconductor substrate, measuring an interference oscillation curve of the X-rays reflected on the semiconductor substrate, and measuring, based on the interference oscillation curve, a concentration of an element adhered on the surface of the semiconductor substrate and/or segregated in an interface of the film.

7. A semiconductor device fabrication method comprising the steps of:

forming a silicon oxide film on a silicon substrate;

nitridizing the silicon substrate with the silicon oxide film formed on, and forming an interface layer containing nitrogen on an interface between the silicon substrate and the silicon oxide film; and irradiating X-rays to the substrate, measuring an interference oscillation curve of the X-rays reflected on the silicon substrate with the silicon oxide film formed on, and measuring a nitrogen concentration in the interface layer, based on the interference oscillation curve.

* * * * *

UNITED STATES PATENT AND TRADEMARK OFFICE
CERTIFICATE OF CORRECTION

PATENT NO. : 6,040,198  
DATED : March 21, 2000  
INVENTOR(S) : Naoki Awaji

It is certified that error appears in the above-identified patent and that said Letters Patent is hereby corrected as shown below:

<u>Title page,</u>
Item [75], Inventors, delete inventors "Satoshi Komiya; Shunji Kashiwagi" both of Kawasaki, Japan.

Signed and Sealed this

Twenty-ninth Day of June, 2004

JON W. DUDAS
*Acting Director of the United States Patent and Trademark Office*